(12) United States Patent
Tian et al.

(10) Patent No.: US 11,731,922 B2
(45) Date of Patent: Aug. 22, 2023

(54) METHOD FOR SEPARATING AROMATIC HYDROCARBON USING EXTRACTIVE DISTILLATION

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Longsheng Tian, Beijing (CN); Ming Zhao, Beijing (CN); Wencheng Tang, Beijing (CN); Siliang Gao, Beijing (CN); Nan Yang, Beijing (CN); Zhifeng Bian, Beijing (CN); Siyuan Qie, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

(*) Notice: Subject to any disclaimer, the term of this patent is extended or adjusted under 35 U.S.C. 154(b) by 373 days.

(21) Appl. No.: 16/964,665

(22) PCT Filed: Jan. 30, 2019

(86) PCT No.: PCT/CN2019/073864
§ 371 (c)(1),
(2) Date: Jul. 24, 2020

(87) PCT Pub. No.: WO2019/149212
PCT Pub. Date: Aug. 8, 2019

(65) Prior Publication Data
US 2021/0053893 A1    Feb. 25, 2021

(30) Foreign Application Priority Data
Feb. 1, 2018 (CN) .......................... 201810101427.9

(51) Int. Cl.
C07C 7/08 (2006.01)
B01D 3/10 (2006.01)
(Continued)

(52) U.S. Cl.
CPC .................. *C07C 7/08* (2013.01); *B01D 3/10* (2013.01); *B01D 3/143* (2013.01); *B01D 3/40* (2013.01);
(Continued)

(58) Field of Classification Search
CPC .. C07C 7/08; C07C 7/005; B01D 3/10; B01D 3/143; B01D 3/40; B01D 11/0492; B01D 2011/002
See application file for complete search history.

(56) References Cited

U.S. PATENT DOCUMENTS 3,844,902 A * 10/1974 Vickers .................... B01D 3/40
585/839
6,375,802 B1   4/2002 Gentry et al.
(Continued)

FOREIGN PATENT DOCUMENTS

CN       1278291 A     12/2000
CN       1541988 A     11/2004
(Continued)

OTHER PUBLICATIONS

International Search Report of International Application No. PCT/CN2019/073864, dated May 7, 2019.
(Continued)

*Primary Examiner* — Youngsul Jeong
(74) *Attorney, Agent, or Firm* — Finnegan Henderson Farabow Garrett & Dunner LLP

(57) ABSTRACT

A method for separating aromatic hydrocarbons by an extractive distillation, comprising introducing a hydrocar-
(Continued)

bon mixture containing aromatic hydrocarbons into the middle of an extractive distillation column (8); introducing an extraction solvent into the upper part of the extractive distillation column; after an extractive distillation, a raffinate containing benzene is discharged from the top of the column, wherein the benzene content is 3-40% by mass, and sent to the lower part of the extraction column (10); the extraction solvent is introduced to the upper part of the extraction column for a liquid-liquid extraction; a raffinate liquid free of aromatic hydrocarbons is discharged from the top of the extraction column; a rich solvent containing benzene is discharged from the bottom of the column and enters the upper-middle part of the extractive distillation column; the rich solvent obtained at the bottom of the extractive distillation column is sent to the solvent recovery column to separate the aromatic hydrocarbons and the solvent. By combining an extractive distillation with a liquid-liquid extraction ingeniously, the method can achieve the separation of aromatic hydrocarbons with a high purity and a high recovery rate, and a significant decrease of the energy consumption in the extraction and separation process.

14 Claims, 1 Drawing Sheet

(51) Int. Cl.
*B01D 3/14* (2006.01)
*B01D 11/04* (2006.01)
*B01D 3/40* (2006.01)
*C07C 7/00* (2006.01)
*B01D 11/00* (2006.01)

(52) U.S. Cl.
CPC .......... *B01D 11/0492* (2013.01); *C07C 7/005* (2013.01); *B01D 2011/002* (2013.01)

(56) References Cited

U.S. PATENT DOCUMENTS 6,565,742 B1 * 5/2003 Gentry .................. C10G 53/06
585/807
2009/0255853 A1 10/2009 Lee et al.

FOREIGN PATENT DOCUMENTS

| CN | 1660970 | A | 8/2005 |
| CN | 103232317 | A | 8/2013 |
| CN | 107001189 | A | 8/2017 |
| RU | 2006126676 | A | 1/2008 |
| TW | 438882 | B | 6/2001 |
| TW | 200942515 | A | 10/2009 |

OTHER PUBLICATIONS

Extended European Search Report for EP19748272.2, dated Oct. 9, 2021.

* cited by examiner

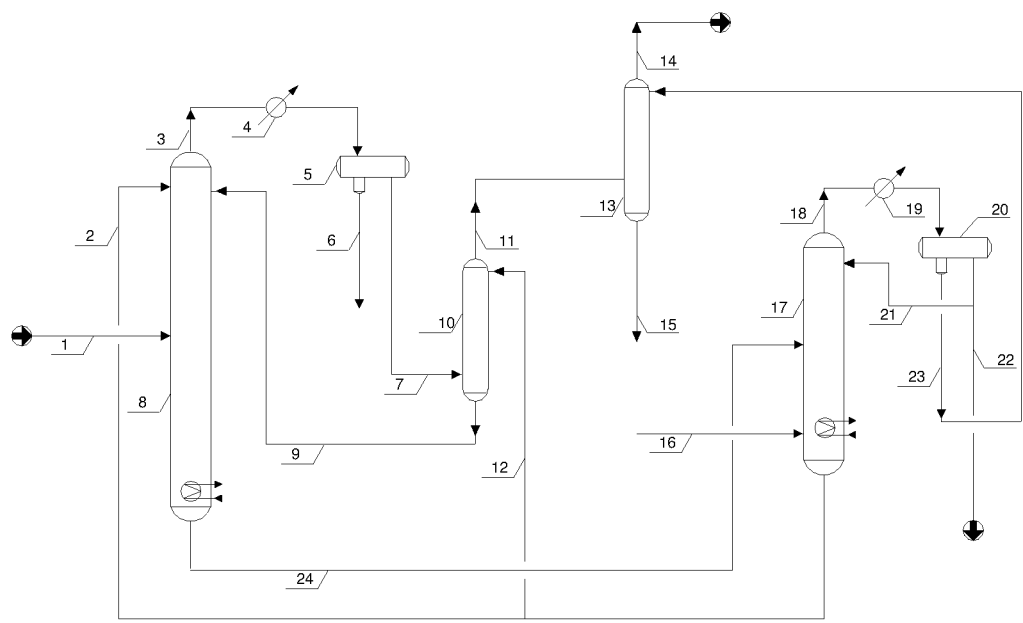

METHOD FOR SEPARATING AROMATIC HYDROCARBON USING EXTRACTIVE DISTILLATION

This application is a national stage filing under 35 U.S.C. § 371 of International Application No. PCT/CN2019/073864, filed Jan. 30, 2019, and claims the priority benefit of Chinese Patent Application No. 201810101427.9, filed Feb. 1, 2018, which are incorporated herein by reference in their entireties.

TECHNICAL FIELD

The present invention relates to a method for separating aromatic hydrocarbons by an extractive distillation, in particular to a method for separating aromatic hydrocarbons by a combined process of an extractive distillation and a liquid-liquid extraction.

BACKGROUND OF THE TECHNOLOGY

There are mainly two methods for separating light aromatic hydrocarbons, i.e., benzene (B), toluene (T) and xylene (X), from a hydrocarbon mixture. One is a liquid-liquid extraction process, which is substantively a combination of a liquid-liquid extraction and a stripping section of an extractive distillation (also known as a stripping column). The other is an extractive distillation method. A BTX-rich hydrocarbon mixture usually includes a catalytic reformate, a hydrogenated pyrolysis gasoline, and tar-crude benzene in the coking industry, wherein the content of BTX aromatic hydrocarbons in the hydrogenated pyrolysis gasoline or in the tar-crude benzene is generally equal to or more than 80%. The contents of $C_8$ cycloalkanes in the above two are 0.5-1% by weight and 0.2-0.5% by weight respectively. There are relatively large differences in the specifications when different extraction and purification processes are adopted.

For the liquid-liquid extraction method, a hydrocarbon mixture is fed from the lower part of the extraction column. A rich solvent stream rich in aromatic hydrocarbons flows into the stripping column for a further separation of the aromatic hydrocarbons and the non-aromatic hydrocarbons. The advantage of this method is that it is applicable to a raw material of wide fractions and it can obtain BTX having a high purity, wherein the content of the non-aromatic hydrocarbons is less than 0.2% by weight and the content of $C_8^+$ cycloalkanes is less than 0.15% by weight. After distillation of the resulting aromatic hydrocarbons, the purities of benzene and toluene may reach the general requirement of the market of 99.9% by mass or more, the purity of the mixed xylene may also reach 99.5% by mass or more, and the BTX content in the raffinate oil is generally less than 1% by mass. The major disadvantage of this method is that when it is applied in a raw material having a high content of aromatic hydrocarbons, such as a hydrogenated pyrolysis gasoline and tar-crude benzene, it is not only necessary to recycle a part of the separated non-aromatic hydrocarbon raffinate oil to the raw material to properly dilute the raw material and maintain the normal operation of the extraction column, but also necessary for the stripping column to evaporate a large amount of backwashing liquids (also known as refluxed aromatic hydrocarbons) which return back to the bottom of the extraction column. Generally, the mass ratio of the backwashing liquids to the feedstock to be extracted generally needs to reach 0.6-1.0 to ensure the purity of the BTX. Therefore, the energy consumption is very high.

Compared with the liquid-liquid extraction, the extractive distillation has the advantages of a simple process and operation, a low device investment and a low energy consumption. However, the existing process for separating aromatic hydrocarbons by an extractive distillation is applicable to the treatment of narrow fractions, such as $C_6$, $C_6$-$C_7$ and $C_8$ fractions, etc. That is, a prefractionation of the raw materials is required. For raw materials such as the hydrogenated pyrolysis gasoline and the tar-crude benzene, the prefractionation may lead to increase of the energy consumption in the whole process. Therefore, its technical and economical value is significantly decreased. If the $C_6$-$C_8$ fractions are directly treated by the existing extractive distillation process, under a reasonable solvent ratio, the purity of the mixed aromatic hydrocarbons generally can only reach about 99.0-99.5% by mass. The impurities are basically $C_8^+$ cycloalkanes, wherein the contents of dimethylcyclohexane and ethylcyclohexane are up to about 0.5% by weight.

Generally, the purity of toluene after such a distillation can only reach 99.7% by mass, and the purity of the mixed xylene is lower, reaching only about 97% by mass. If an equivalent purity to the liquid-liquid extraction is desired, a rather high solvent ratio or an expense of the benzene recovery rate is required. The benzene content in the corresponding raffinate oil is up to 5-10% by weight. Therefore, the existing extractive distillation technology exposes large shortcomings and deficiencies in the treatment of the above raw materials of $C_6$-$C_8$ wide fractions.

U.S. Pat. No. 3,844,902 discloses a combined process of an extractive distillation and a liquid-liquid extraction, which is formed by an extractive distillation and a liquid-liquid extraction process connected in series. First, the raw material enters the middle part of the extractive distillation column, and the solvent for the extractive distillation enters the upper part of the extractive distillation column. After the extractive distillation, a rich solvent containing heavy aromatic hydrocarbons enters the solvent recovery column of the extractive distillation system, where the solvent and the heavy aromatic hydrocarbons are separated. After condensation and cooling of the overhead effluents of the extractive distillation column, a part acts as a reflux, and the other part is sent to the liquid-liquid extraction column. The extraction solvent enters from the top of the liquid-liquid extraction column. After extraction and separation, a raffinate oil is discharged from the top of the column; the bottom effluents of the extraction column enter the stripping column for stripping; a backwashing liquid distilled out from the top of the stripping column is sent to the bottom of the extraction column. The rich solvent almost free of non-aromatic hydrocarbons at the bottom of the stripping column enters the solvent recovery column of the extraction unit, where the light aromatic hydrocarbons and the solvent are separated. The overhead effluents of the extractive distillation column contain relatively light aromatic hydrocarbons, including the benzene and a part of the toluene in the raw material. This process, by connecting the extractive distillation and the complete liquid-liquid extraction process in series, may achieve a high purity and a high recovery rate of aromatic hydrocarbons, and also separate aromatic hydrocarbons into light aromatic hydrocarbons and heavy aromatic hydrocarbons. However, the process is long and the investment of the device is high.

CN103232317A discloses an aromatic hydrocarbon purification apparatus and process used in hydrofining of coking crude benzene. N-formyl morpholine (NFM) is used as a solvent, and a method of coupling an extractive distillation and a liquid-liquid extraction is used for separation and purification of the aromatic hydrocarbon. A gaseous condensate at the top of the extractive distillation column and at side lines of levels 1-5 of the upper part of the extractive distillation column is sent to the extraction column; the material at the bottom of the extraction column returns to the top of the extractive distillation column; non-aromatic hydrocarbons are discharged from the top of the extraction column; the rich solvent discharged from the bottom of the extractive distillation column enters the stripping column of aromatic hydrocarbons, where the aromatic hydrocarbons and the solvent are separated.

CN107001189A discloses an extractive distillation process for recovering aromatic hydrocarbons, which employs an extractive distillation column with a novel overhead system including a partial condenser. The process, to a certain extent, strengthens the capability of removing heavy non-aromatic hydrocarbons, particularly $C_8$ naphthenic compounds, from the bottom of the extractive distillation column, increases the purity of aromatic products, especially of the mixed xylenes, reduces the loss of benzene in the raffinate product and, as a result, enhances the benzene recovery. However, in the method, the totally or partially condensed raffinate at the top of the extractive distillation column and the extraction solvent are directly passed through a static mixer or a multi-stage contactor, and then subjected to a phase separation in a separator; a solvent phase containing water and benzene is recycled to a relatively lower portion of the extractive distillation column, and a part of the raffinate acts as the overhead reflux of the extractive distillation column. In such an operation, the content of water and non-aromatic hydrocarbons in the upper portion of the extractive distillation column is excessively high, leading to a decrease of the selectivity to non-aromatic hydrocarbons/benzene. A certain amount of $C_8$ cycloalkanes is also dissolved in the stream recycling to a relatively lower portion of the extractive distillation column and can hardly be distilled out. Therefore, the capability of removing heavy non-aromatic hydrocarbons is not satisfying yet. The non-aromatic hydrocarbons, such as $C_8^+$ cycloalkanes, in the final mixed aromatic hydrocarbons are ≯1% by weight, preferably ≯0.5% by weight. As $C_8$ cycloalkanes can form azeotropes with toluene, the purity of toluene still can hardly reach 99.9% by weight.

CONTENTS OF THE INVENTION

The object of the present invention is to provide a method for separating aromatic hydrocarbons by an extractive distillation. By combining an extractive distillation with a liquid-liquid extraction ingeniously, the method can achieve a separation of aromatic hydrocarbons in a high purity and a high recovery rate, and a decrease of the energy consumption in the extraction and separation process.

The method for separating aromatic hydrocarbons by an extractive distillation provided in the present invention comprises following steps:

(1) introducing a hydrocarbon mixture containing aromatic hydrocarbons into the middle of an extractive distillation column; introducing an extraction solvent into the upper part of the extractive distillation column; after an extractive distillation, a raffinate containing benzene is discharged from the top of the column, wherein the benzene content is 3-40% by mass; and a rich solvent rich in aromatic hydrocarbons is obtained at the bottom of the column, (2) the raffinate discharged from the top of the extractive distillation column is sent to the lower part of an extraction column; the extraction solvent is introduced to the upper part of the extraction column; after a liquid-liquid extraction, a raffinate liquid free of aromatic hydrocarbons is discharged from the top of the extraction column; a rich solvent containing benzene is discharged from the bottom of the column and enters the upper-middle part of the extractive distillation column, which lies between the positions at which the extraction solvent and the raw material are introduced, (3) the rich solvent obtained from the bottom of the extractive distillation column is sent to the middle of a solvent recovery column; after vacuum distillation, the aromatic hydrocarbons are discharged from the top of the solvent recovery column, and a lean solvent is discharged from the bottom of the solvent recovery column.

The method of the present invention distills out a suitable amount of benzene in the overhead effluents of the extractive distillation column, then carries out a liquid-liquid extraction on the effluents, returns the resulting rich solvent containing benzene to the upper-middle part of the extractive distillation column, and then sends the rich solvent obtained at the bottom of the extractive distillation column to the solvent recovery column for separating the aromatic hydrocarbons and the solvent. The method can achieve an efficient separation of the aromatic hydrocarbons from the raw material of wide fractions, allowing the purity of the aromatic hydrocarbons to reach 99.0% by mass or more with a low energy consumption during the process.

DESCRIPTION OF DRAWINGS

FIGURE is a flow diagram for separating aromatic hydrocarbons by an extractive distillation in the present invention.

SPECIFIC EMBODIMENTS

The present invention is mainly based on the operation of an extractive distillation, controls the range of the benzene evaporation amount at the top of the extractive distillation column, and carries out the liquid-liquid extraction on the raffinate containing benzene to further recover benzene; the resulting rich solvent containing benzene from the liquid-liquid extraction is recycled to the upper-middle part of the extractive distillation column; then the aromatic hydrocarbons in the rich solvent obtained from the bottom of extractive distillation column are separated from the solvent. The method can obtain mixed aromatic hydrocarbons of high purity and allow the $C_8$ cycloalkanes in the raw material to enter the raffinate liquid, thereby recovering benzene in the raw material completely. Moreover, the energy consumption in the whole process is relatively low.

Step (1) of the method of the present invention is the extractive distillation of the raw material. In the distillation process, a suitable amount of benzene is charged into the overhead effluents, i.e., obtaining a raffinate containing benzene, so that the $C_8$ cycloalkanes in the raw material substantively enter the raffinate. Preferably, the mass ratio of the raffinate containing benzene discharged from the top of the extractive distillation column to the raw material entering the column is 5-45%, preferably 5-30%, and the benzene content in the raffinate containing benzene is 10-30% by mass.

Preferably, the raffinate containing benzene discharged from the top of the extractive distillation column is condensed and thereafter subjected to an oil-water separation. Then the dehydrated raffinate containing benzene is sent to the lower part of the extraction column.

In Step (1), it is preferred that the upper part of the extractive distillation column is not provided with a raffinate reflux. Instead, the raffinate containing benzene discharged from the top of the extractive distillation column is wholly sent to the extraction column for a liquid-liquid extraction.

The extraction solvent of the present invention is selected from sulfolane, triethylene glycol, tetraethylene glycol, pentaethylene glycol or triethylene glycol monomethyl ether, preferably sulfolane.

The extraction solvent according to the present invention may comprise 0.1-1.0% by mass of water, preferably 0.4-0.8% by mass of water, so as to increase the selectivity of the solvent.

Step (2) of the method of the present invention is the liquid-liquid extraction on the raffinate containing benzene discharged from the top of the extractive distillation column for recovering the benzene therein. A raffinate liquid substantively free of aromatic hydrocarbons is discharged from the top of the extraction column. The content of the aromatic hydrocarbons in the raffinate liquid is preferably no more than 0.5% by mass, more preferably no more than 0.3% by mass. The rich solvent containing benzene at the bottom returns to the upper-middle part of the extractive distillation column, and the position at which the rich solvent enters the extractive distillation column is between the positions at which the extraction solvent and the raw material enter the column. The upper-middle part of the extractive distillation column refers to the region between the positions at which the extraction solvent and the raw material enter the column, where the region close to the position at which the extraction solvent is introduced is the upper part and the rest portion is the middle part. Preferably, the rich solvent containing benzene is introduced to the $1^{st}$-$20^{th}$, preferably the $2^{nd}$-$9^{th}$ theoretical plates, downstream of the position at which the extraction solvent is introduced in the extractive distillation column.

Preferably, the raffinate liquid discharged from the top of the extraction column is washed with water; the water washing is carried out in a water washing column; the raffinate liquid after the water washing is discharged out of the system; the water after the washing is stripped to remove the trace non-aromatic hydrocarbons therein and then used as a stripping medium. The water washing temperature is preferably 35-45° C.

Step (3) of the method of the present invention is sending the rich solvent rich in aromatic hydrocarbons discharged from the bottom of the extractive distillation column into the solvent recovery column to separate the aromatic hydrocarbons and the solvent. Preferably, the lean solvent obtained in Step (3) is respectively returned to the upper parts of the extractive distillation column and the extraction column for reuse.

The theoretical plate number of the extractive distillation column according to Step (1) of the present invention is preferably 25-60; the temperature at the bottom of the column is preferably 140-185° C.; the overhead pressure is preferably 0.1-0.4 MPa; the overhead temperature is preferably 110-135° C. Preferably, the temperature of the extraction solvent entering the extractive distillation column is controlled at 80-130° C., and the volume ratio(solvent ratio) of the extraction solvent entering the extractive distillation column to the raw material for the extractive distillation is 2.0-5.5.

The theoretical plate number of the extraction column according to Step (2) is preferably 3-30; the temperature of the extraction solvent entering the column is preferably 40-90° C.; the volume ratio(solvent ratio) of the extraction solvent to the raw material to be extracted is preferably 1-3.

The theoretical plate number of the solvent recovery column according to Step (3) is preferably 8-28; the overhead pressure is preferably 0.02-0.1 MPa, more preferably 0.02-0.08 MPa; the overhead reflux ratio, i.e., the mass ratio of the refluxed material to the material discharged from the top of the column is preferably 0.3-1.0; the overhead temperature is preferably 50-80° C., and the temperature at the bottom of the column is preferably 150-185° C.

The pressures of the present invention are all absolute pressures.

The content of the aromatic hydrocarbons in the hydrocarbon mixture of the present invention may be 60-98% by mass, preferably 70-98% by mass. The hydrocarbon mixture may be $C_6$-$C_8$ fractions of a catalytic reformate, ethylene cracking hydrogenated gasoline or tar-crude benzene.

The present invention also provides a device for separating aromatic hydrocarbons by an extractive distillation, comprising an extractive distillation column, an extraction column and a solvent recovery column; the upper parts of the extractive distillation column and the extraction column are both provided with lines for injection of the extraction solvent; the middle of the extractive distillation column is provided with a line for feeding a hydrocarbon mixture containing aromatic hydrocarbons; the top is provided with a line for discharging the raffinate containing benzene; the line for discharging the raffinate is connected with the lower part of the extraction column; the top of the extraction column is provided with a line for discharging a raffinate liquid; the bottom of the column is provided with a line in connection with the upper-middle part of the extractive distillation column for returning the rich solvent containing benzene; the bottom of the extractive distillation column is provided with a line for discharging the rich solvent in connection with the middle of the solvent recovery column; the top of the solvent recovery column is provided with a line for discharging the aromatic hydrocarbons; the line for discharging a lean solvent at the bottom of the solvent recovery column is respectively connected with the lines for injecting the extraction solvent in the upper parts of the extractive distillation column and the extraction column.

Preferably, the device is further provided with a water washing column for the raffinate liquid, the top of which is provided with a line for discharging the raffinate liquid after water washing, the bottom of which is provided with a line for discharging the water after water washing, and the upper part of which is provided with a line for injecting the water for water washing.

Preferably, the top line of the extractive distillation column is connected with a separator for separating water; the separator is provided with a line for discharging the water and a line for discharging the dehydrated raffinate; the line for discharging the dehydrated raffinate is connected with the lower part of the extraction column.

Preferably, the overhead line of the solvent recovery column is connected with a reflux tank which is provided with a line for discharging the water and a line for discharging the dehydrated aromatic hydrocarbons; the line for discharging the dehydrated aromatic hydrocarbons is provided with a reflux line.

The present invention is illustrated in details in combination with the figures.

In the FIGURE, the hydrocarbon mixture containing aromatic hydrocarbons enters the middle of the extractive distillation column 8 via line 1; the extraction solvent enters the upper part of the extractive distillation column via line 2. After the extractive distillation, the raffinate containing benzene is discharged from the overhead line 3 of the extractive distillation column and then enters the condenser 4. The condensed and cooled stream enters the separator 5. After an oil-water separation, water containing a small amount of solvent is discharged via line 6, and the raffinate containing benzene is sent to the lower part of the extraction column 10 via line 7; the extraction solvent enters the upper part of the extraction column 10 via line 12; an extraction and separation is carried out by a countercurrent liquid phase contact in the extraction column. The raffinate liquid substantively free of aromatic hydrocarbons is introduced to the lower part of the water washing column 13 for the raffinate via line 11; water from line 23 is introduced into the water washing column from the upper part; the raffinate liquid product obtained after water washing is discharged out of the device via line 14; the water after the washing is discharged via line 15. The rich solvent containing benzene discharged from the bottom of the extraction column 10 returns to the upper part, or the middle, of the extractive distillation column via line 9.

The rich solvent containing aromatic hydrocarbons at the bottom of the extractive distillation column is sent to the middle of the solvent recovery column 17 via line 24; the stripping water or the steam is introduced to the lower part of the solvent recovery column 17 via line 16; after vacuum stripping, the aromatic hydrocarbons and the steam are discharged from the top of the column and enter condenser 19 via line 18, and after condensation and cooling, enter the reflux tank 20; after an oil-water separation, a part of the oil phase flows back to the upper part of the solvent recovery column via line 21 and the rest of the oil phase is discharged as the mixed aromatic hydrocarbons via line 22; the lean solvent obtained after the separation of the aromatic hydrocarbons is discharged from the bottom of the solvent recovery column; after heat exchange and temperature controlling by cooling, most of the lean solvent is recycled to the upper part of the extractive distillation column, and a small part acts as the extraction solvent of the extraction column.

The present invention is further explained with the examples. However, the present invention is not limited by these examples.

Example 1

According to the process of the FIGURE, a pure BTX was recovered by an extractive distillation from the raw material of $C_6$-$C_8$ fractions of the hydrogenated pyrolysis gasoline, with the water-containing sulfolane as the extraction solvent. See Table 1 for the composition of the employed raw material. The benzene content in the raffinate discharged from the top of the column during the extractive distillation process was controlled at 15% by mass. See Table 2 for the main operation conditions and the water content of the lean solvent. See Table 3 for the extractive distillation and the results after the BTX separation by the distillation. The rich solvent containing benzene after the liquid-liquid extraction returned to the $3^{rd}$ theoretical plate in the upper part of the extractive distillation column. The position at which the lean solvent entered the column was the $1^{st}$ theoretical plate; the position at which the raw material entered the column was the $13^{th}$ theoretical plate. The temperature for the water washing of the raffinate liquid discharged from the top of the extraction column was 40° C.

Example 2

$C_6$-$C_8$ fractions of the tar-crude benzene were used as the raw material. See Table 1 for the composition BTX was recovered by the extractive distillation according to the method of Example 1, except that the benzene content in the raffinate discharged from the top of the column during the extractive distillation process was controlled at 23.8% by mass. The rich solvent containing benzene after the liquid-liquid extraction returned to the $5^{th}$ theoretical plate in the upper part of the extractive distillation column. See Table 2 for the main operation conditions and the water content of the lean solvent. See Table 3 for the results of the extractive distillation and the BTX separation by the distillation.

Example 3

BTX was recovered by the extractive distillation according to the method of Example 1, except that the top of the extractive distillation column was provided with a raffinate reflux. The raffinate flew back to the $1^{st}$ theoretical plate in the upper part of the column with a reflux ratio (the mass ratio of the refluxed material to the material discharged from the top of the column) of 0.20. See Table 2 for the main operation conditions. See Table 3 for the results of the extractive distillation and the separation by the distillation.

Comparative Example 1

BTX was recovered by an extractive distillation of the raw material according to Example 1 in a conventional extractive distillation method. The device was not provided with an extraction column and a water washing column. The rest was substantively the same as the FIGURE, except that after an oil-water separation, a part of the overhead effluents of the extractive distillation column was sent to the $1^{st}$ theoretical plate in the upper part of the column as a reflux. The rest was discharged out of the system as a raffinate oil. See Table 2 for the main operation conditions. See Table 3 for the results of the extractive distillation and the BTX separation by the distillation.

Comparative Example 2

BTX was recovered by an extractive distillation according to the method of Example 1, except that the rich solvent containing benzene after the extraction returned to the $27^{th}$ theoretical plate in the lower part of the extractive distillation column. See Table 2 for the main operation conditions. See Table 3 for the results of the extractive distillation and the separation by the distillation.

Comparative Example 3

The raw material and the solvent of Example 1 were used. According to the method of CN103232317A, the overhead gas phase of the extractive distillation column and the gas phase discharged from the side line of the $3^{rd}$ theoretical plate were mixed and then condensed, and after that, were sent to the extraction column for recovering benzene by a liquid phase extraction. Moreover, the rich solvent containing benzene at the bottom of the extraction column was returned to the top of the extractive distillation column. See Table 2 for the main operation conditions. See Table 3 for the results of the extractive distillation and the separation by the distillation.

It can be seen from the data in Table 3 that, in the mixed aromatic hydrocarbons obtained by the method of the present invention, the content of $C_8$ cycloalkanes is as low as 0.019-0.054% by mass, the content of $C_8$ and $C_9+$ cycloalkanes is ≯0.16% by mass; the benzene content in the raffinate liquid is as low as about 0.1% by mass; the content of the aromatic hydrocarbons is as low as 0.3% by mass or lower. It shows that the recovery of benzene was full and the recovery of toluene and xylene was also relatively full. After the distillation, the purities of the B, T and X products reached 99.99% by mass, 99.90-99.93% by mass and 99.0% by mass, respectively. All of the above meet or are superior to the requirements on the highest product specifications of the market. The purities are greatly improved compared to the purities of BTX separated in Comparative Examples 1-3.

TABLE 1

| composition | $C_6$-$C_8$ fractions of hydrogenated pyrolysis gasoline | $C_6$-$C_8$ fractions of tarcrude benzene |
|---|---|---|
| alkane, % by mass | | |
| $C_5$ | 0.00 | 0.19 |
| $C_6$ | 1.19 | 0.11 |
| $C_7$ | 1.47 | 0.11 |
| $C_8^+$ | 0.48 | 0.21 |
| cycloalkanes, % by mass | | |
| $C_5$ | 0.30 | 0.87 |
| $C_6$ | 5.00 | 0.62 |
| $C_7$ | 1.54 | 0.16 |
| $C_8$ | 0.80 | 0.15 |
| $C_9^+$ | 0.10 | 0.02 |
| aromatic hydrocarbons, % by mass | | |
| $C_6$ | 51.67 | 75.65 |
| $C_7$ | 26.21 | 16.36 |
| $C_8$ | 11.24 | 5.55 |
| $C_9^+$ | 0.000 | 0.00 |

TABLE 2

| items | Example 1 | Example 2 | Example 3 | Comparative Example 1 | Comparative Example 2 | Comparative Example 3 |
|---|---|---|---|---|---|---|
| extractive distillation column | | | | | | |
| theoretical plate number | 30 | 30 | 35 | 35 | 30 | 30 |
| ordinal number of the theoretical plate which the raw material entered* | 13 | 13 | 18 | 18 | 13 | 13 |
| solvent ratio (to the raw material, by volume) | 3.8 | 4.6 | 3.8 | 3.9 | 3.8 | 3.8 |
| reflux ratio (to the material discharged from the top of the column, by mass) | — | — | 0.2 | 0.3 | 0.25 | — |
| overhead pressure, MPa | 0.16 | 0.20 | 0.16 | 0.16 | 0.16 | 0.16 |
| temperature of the solvent entering the column, °C. | 110 | 102 | 110 | 110 | 110 | 110 |
| ordinal number of the theoretical plate which the solvent entered | 1 | 1 | 6 | 6 | 1 | 1 |
| mass ratio of the raffinate discharged from the top of the column/raw material entering the column, % | 16.1 | 5.2 | 16.9 | 16.0 | 16.6 | 16.1 |
| benzene content in the raffinate discharged at the top of the column, % by mass | 15.0 | 23.8 | 13.0 | 5.8 | 12.0 | 15.0 |
| ordinal number of the theoretical plate to which the rich solvent containing benzene returns | 3 | 5 | 8 | — | 27 | 1 |
| overhead temperature of the column, °C. | 124 | 126 | 123 | 102 | 123 | 124 |
| temperature at the bottom of the column, °C. | 170 | 169 | 170 | 171 | 170 | 170 |
| extraction column | | | | | | |
| theoretical plate number | 8 | 8 | 8 | — | 8 | 8 |
| solvent ratio (to the raw material, by volume) | 1.3 | 1.4 | 1.3 | — | 1.3 | 1.3 |
| temperature of the solvent entering the column, °C. | 65 | 65 | 65 | — | 65 | 65 |

TABLE 2-continued

| items | Example 1 | Example 2 | Example 3 | Comparative Example 1 | Comparative Example 2 | Comparative Example 3 |
|---|---|---|---|---|---|---|
| solvent recovery column | | | | | | |
| theoretical plate number | 12 | 12 | 12 | 12 | 12 | 12 |
| overhead pressure, MPa | 0.04 | 0.04 | 0.04 | 0.04 | 0.04 | 0.04 |
| reflux ratio (to the material discharged from the top of the column, by mass) | 0.6 | 0.6 | 0.6 | 0.6 | 0.6 | 0.6 |
| overhead temperature of the column, °C. | 72 | 66 | 72 | 73 | 72 | 72 |
| temperature at the bottom of the column, °C. | 173 | 171 | 173 | 173 | 173 | 173 |
| water content of the lean solvent, % by mass | 0.6 | 0.7 | 0.6 | 0.6 | 0.6 | 0.6 |

The theoretical plate ordinal number of the extractive distillation column refers to the sequence number from the top to the bottom

TABLE 3

| items | Example 1 | Example 2 | Example 3 | Comparatative Example 1 | Comparative Example 2 | Comparative Example 3 |
|---|---|---|---|---|---|---|
| content of $C_8$ cycloalkanes in the mixed aromatic hydrocarbons, % by mass | 0.035 | 0.019 | 0.054 | 0.290 | 0.122 | 0.117 |
| content of $C_9^+$ cycloalkanes in the mixed aromatic hydrocarbons, % by mass | 0.093 | 0.021 | 0.101 | 0.112 | 0.106 | 0.099 |
| benzene content in the raffinate liquid, % by mass | 0.087 | 0.120 | 0.087 | 5.80 | 0.082 | 0.087 |
| content of aromatic hydrocarbons in the raffinate liquid, % by mass | 0.237 | 0.280 | 0.200 | 6.28 | 0.210 | 0.240 |
| purity of benzene after the distillation, % by mass | 99.99 | 99.99 | 99.99 | 99.97 | 99.99 | 99.99 |
| purity of toluene after the distillation, % by mass | 99.93 | 99.96 | 99.90 | 99.70 | 99.78 | 99.81 |
| purity of xylene after the distillation, % by mass | 99.04 | 99.61 | 99.00 | 97.65 | 98.57 | 98.71 |
| heat load in the extractive distillation, $10^9$ J/ton of feedstock | 1.150 | 1.180 | 1.156 | 1.151 | 1.160 | 1.150 |

The invention claimed is:

1. A method for separating aromatic hydrocarbons by an extractive distillation, comprising following operations:
   (1) introducing a hydrocarbon mixture containing aromatic hydrocarbons into middle part of an extractive distillation column; introducing an extraction solvent into upper part of the extractive distillation column; after an extractive distillation, discharging a raffinate containing benzene from the top of the extractive distillation column, wherein the benzene content in the raffinate is 3-40% by mass; and a rich solvent rich in aromatic hydrocarbons is obtained at the bottom of the extractive distillation column,
   (2) sending the raffinate discharged from the top of the extractive distillation column to lower part of an extraction column; introducing the extraction solvent into upper part of the extraction column; after a liquid-liquid extraction, discharging a raffinate liquid free of aromatic hydrocarbons from the top of the extraction column; discharging a rich solvent containing benzene from the bottom of the extraction column and introducing the rich solvent containing benzene into upper-middle part of the extractive distillation column, which lies between the positions at which the extraction solvent and the hydrocarbon mixture are introduced, wherein the rich solvent containing benzene is introduced to the $2^{nd}$-$9^{th}$ theoretical plates downstream of the position at which the extraction solvent is introduced in the extractive distillation column, and
   (3) sending the rich solvent rich in aromatic hydrocarbons obtained from the bottom of the extractive distillation column to middle part of a solvent recovery column; after a vacuum distillation, discharging a streaming comprising aromatic hydrocarbons from the top of the solvent recovery column, and discharging a lean solvent from the bottom of the solvent recovery column.

2. The method according to claim 1, characterized in that a mass ratio of the raffinate containing benzene discharged from the top of the extractive distillation column to the hydrocarbon mixture entering the extractive distillation column is 5-45%, wherein the benzene content in the raffinate containing benzene is 10-30% by mass.

3. The method according to claim 1, characterized in that the extraction solvent is selected from sulfolane, triethylene glycol, tetraethylene glycol, pentaethylene glycol and triethylene glycol monomethyl ether.

4. The method according to claim 1, characterized in that the extraction solvent comprises 0.1-1.0% by mass of water.

5. The method according to claim 1, characterized in that the extraction solvent comprises 0.4-0.8% by mass of water.

6. The method according to claim 1, characterized in that in operation (1), the raffinate containing benzene discharged from the top of the extractive distillation column is condensed and thereafter subjected to an oil-water separation to obtain a dehydrated raffinate; then the dehydrated raffinate containing benzene is sent to the bottom of the extraction column.

7. The method according to claim 1, characterized in that in operation (1), the upper part of the extractive distillation column is not provided with a raffinate reflux.

8. The method according to claim 1, characterized in that the raffinate liquid discharged from the top of the extraction column in operation (2) is washed with water.

9. The method according to claim 1, characterized in that the lean solvent obtained in operation (3) is respectively returned to the upper parts of the extractive distillation column and the extraction column for reuse.

10. The method according to claim 1, characterized in that a theoretical plate number of the extractive distillation column in operation (1) is 25-60; a temperature at the bottom of the extractive distillation column is 140-185° C.; and an overhead pressure of the extractive distillation column is 0.1-0.4 MPa.

11. The method according to claim 10, characterized in that a temperature of the extraction solvent introduced into the extractive distillation column is controlled at 80-130° C., and a volume ratio of the extraction solvent introduced into the extractive distillation column to the hydrocarbon mixture is 2.0-5.5.

12. The method according to claim 1, characterized in that a theoretical plate number of the extraction column in operation (2) is 3-30; a temperature of the extraction solvent introduced into the extraction column is 40-90° C.; and a volume ratio of the extraction solvent introduced into the upper part of the extraction column to the raffinate containing benzene discharged from top of the extractive distillation column is 1-3.

13. The method according to claim 1, characterized in that a theoretical plate number of the solvent recovery column in operation (3) is 8-28; an overhead pressure of the of the solvent recovery column is 0.02-0.1 MPa; an overhead reflux ratio of the of the solvent recovery column is 0.3-1.0; an overhead temperature of the of the solvent recovery column is 50-80° C.; and a temperature at the bottom of the solvent recovery column is 150-185° C.

14. The method according to claim 1, characterized in that a content of the aromatic hydrocarbons in the hydrocarbon mixture is 60-98% by mass.

\* \* \* \* \*

UNITED STATES PATENT AND TRADEMARK OFFICE
CERTIFICATE OF CORRECTION

PATENT NO. : 11,731,922 B2
APPLICATION NO. : 16/964665
DATED : August 22, 2023
INVENTOR(S) : Longsheng Tian et al.

It is certified that error appears in the above-identified patent and that said Letters Patent is hereby corrected as shown below:

In the Claims

Claim 13, Column 14, Lines 21-22, "pressure of the of the solvent" should read --pressure of the solvent--.

Claim 13, Column 14, Line 23, "ratio of the of the solvent" should read --ratio of the solvent--.

Claim 13, Column 14, Line 24, "temperature of the of the solvent" should read --temperature of the solvent--.

Signed and Sealed this
Twenty-fourth Day of October, 2023

Katherine Kelly Vidal
*Director of the United States Patent and Trademark Office*